United States Patent
Igaki et al.

(10) Patent No.: US 6,823,860 B2
(45) Date of Patent: Nov. 30, 2004

(54) STEAM-GENERATING HEATING SHEET FOR THE EYES

(75) Inventors: Michihito Igaki, Tokyo (JP); Takeshi Oka, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/358,162

(22) Filed: Feb. 5, 2003

(65) Prior Publication Data

US 2004/0035410 A1 Feb. 26, 2004

(30) Foreign Application Priority Data

Aug. 21, 2002 (JP) ........................................ 2002-241135

(51) Int. Cl.[7] .................................................. F24J 1/00
(52) U.S. Cl. .................................. 126/263.05; 607/109
(58) Field of Search ...................... 126/263.05, 263.06, 126/263.04, 263.01, 204; 607/109, 114; 165/46

(56) References Cited

U.S. PATENT DOCUMENTS

| | | | | |
|---|---|---|---|---|
| 2,318,420 A | * | 5/1943 | Racen .................... | 126/263.05 |
| RE32,026 E | * | 11/1985 | Yamashita et al. ..... | 126/263.02 |
| 4,573,447 A | * | 3/1986 | Thrash et al. .......... | 126/263.06 |
| 4,756,299 A | * | 7/1988 | Podella .................. | 126/263.02 |
| 5,233,981 A | * | 8/1993 | Miyashita .................... | 607/114 |
| 5,376,392 A | * | 12/1994 | Ikegami et al. ............. | 426/127 |
| 5,975,074 A | * | 11/1999 | Koiso et al. ........... | 126/263.02 |
| 6,409,746 B1 | | 6/2002 | Igaki et al. ................. | 607/109 |

FOREIGN PATENT DOCUMENTS

| | | | | |
|---|---|---|---|---|
| EP | 1 090 614 | | 4/2001 | |
| EP | 1 147 752 | | 10/2001 | |
| EP | 1 264 585 | | 12/2002 | |
| JP | 8-84667 A | * | 4/1996 | .............. F24J/1/00 |
| JP | 2001-170096 | | 6/2001 | |
| JP | 2001-245915 | | 9/2001 | |

* cited by examiner

Primary Examiner—Josiah Cocks
(74) Attorney, Agent, or Firm—Oblon, Spivak, McClelland, Maier & Neustadt, P.C.

(57) ABSTRACT

An eye-use steam-generating heating sheet contains a steam-generating composition, which is covered with at least a first moisture-permeable sheet and a second moisture-permeable sheet in that order. The first moisture-permeable sheet has a moisture permeability of at least 600 $g/m^2/24$ hrs, the second moisture-permeable sheet has a moisture permeability has a moisture permeability of 700 to 3000 $g/m^2/24$ hrs, the first moisture-permeable sheet and the second moisture-permeable sheet are provided such that a steam accumulation space is formed therebetween, and at least one of the moisture-permeable sheets covering the steam-generating composition has a water resistance of at least 400 mm. This eye-use steam-generating heating sheet is sealed for storage.

9 Claims, 3 Drawing Sheets

FIG. 5

STEAM-GENERATING HEATING SHEET FOR THE EYES

BACKGROUND OF THE INVENTION

1. Field of the Invention

The present invention relates to a steam-generating heating sheet for the eyes, which supplies modest heat and steam to the eyes and the area around the eyes in order to relieve eyestrain, alleviate dryness of the eyes, and provide a pleasant sensation.

2. Description of the Related Art

In the past, modest heat and steam was supplied to the eyes and around the eyes by using a steamed towel in order to relieve eyestrain and alleviate dryness of the eyes. Eye pillows have also been proposed, which make use of a steam-generating composition composed of a heat-generating material commonly referred to as a chemical pocket warmer, so that the user can supply modest heat and steam to and around the eyes easily and whenever necessary (Japanese Laid-Open Patent Applications 2001-170096 and 2001-245915 and elsewhere).

The eyes and the area around the eyes (particularly the thin skin of the eyelids) are very sensitive to heat, and the eyes are an organ that does not readily regenerate once damaged. If the steam released from a steam-generating composition is supplied directly to the eyes, there may occur a problem on safety because of the high temperature of the steam. Consequently, controlling the temperature of the steam released from the steam-generating composition is very important for an eye pillow that makes use of a steam-generating composition. In view of this, with conventional eye pillows that contained a steam-generating composition, in order to control the temperature of the steam supplied to the eyes, the steam-generating composition was housed in a moisture permeability pouch, after which a number of layers of nonwoven cloth, paper, or the like were laid over this as temperature buffers.

However, using several layers of temperature buffers made the eye pillow thicker and bulkier, and applying an eye pillow such as this over the eyes or around the eyes caused the wearer some discomfort because the pillow did not conform well to the unevenness around the eyes. Also, such eye pillows were more difficult to carry around, more inefficient to distribute for sale, and more expensive to manufacture. Another problem was that the paper or the like used as a temperature buffer would yellow during long-term storage, which diminished the commercial value of the product.

SUMMARY OF THE INVENTION

It is an object of the present invention to provide a steam-generating heating sheet for the eyes, which is thin thickness, can be manufactured inexpensively, and allows modest heat and steam to be supplied safely to the eyes and around the eyes.

The inventors have discovered that when a steam-generating composition is covered with a moisture-permeable sheet and steam is generated, if two or more moisture-permeable sheets are used on the steam generation side and the moisture permeability of these sheets is controlled so that a steam accumulation space is formed between the two moisture-permeable sheets, the steam can be kept at a temperature that is safe for the eyes, without using several layers of temperature buffer, and the steam temperature can be made more uniform so that the entire application surface is more evenly warmed, and therefore a steam-generating heating sheet for the eyes that is in the form of a thin sheet suited to application over the eyes and the area around the eyes can be produced at a low cost.

Specifically, the present invention provides a steam-generating heating sheet for the eyes, in which a steam-generating composition is contained, said steam-generating composition is covered with at least a first moisture-permeable sheet and a second moisture-permeable sheet in that order, and the steam-generating heating sheet for the eyes is stored in airtight container until use, wherein the first moisture-permeable sheet has a moisture permeability (ASTM E-96-80D method) of at least 600 $g/m^2/24$ hrs;

the second moisture-permeable sheet has a moisture permeability (ASTM E-96-80D method) of 700 to 3000 $g/m^2/24$ hrs;

the first moisture-permeable sheet and the second moisture-permeable sheet are provided such that a steam accumulation space is formed therebetween; and at least one of the moisture-permeable sheets covering the steam-generating composition has a water resistance of at least 400 mm.

BRIEF DESCRIPTION OF THE DRAWINGS 1A indicates the eye-use steam-generating heating sheet.

FIG. 1-$x$ is a plan view of the eye-use steam-generating heating sheet (1A) of the present invention in airtight container 7, FIG. 1-$y$ is a cross section of the eye-use steam-generating heating sheet of the present invention in airtight container 7 and FIG. 1-$z$ is a cross section of the eye-use steam-generating heating sheet of the present invention when the steam is released after the eye-use steam-generating heating sheet is removed from its airtight container;

DETAILED DESCRIPTION OF THE INVENTION

The present invention will now be described in detail through reference to the drawings. In the drawings, the same reference symbols denote same or similar constituent elements.

Figure 1X:
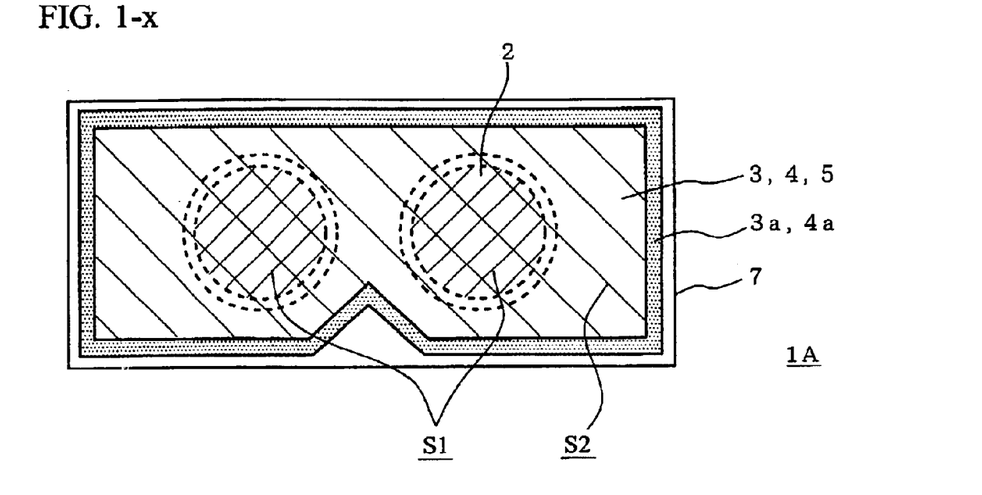
Figure 1Y:
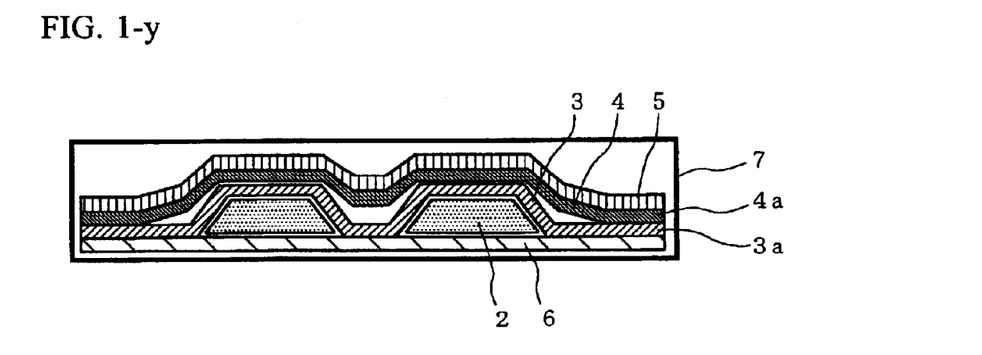
Figure 1Z:
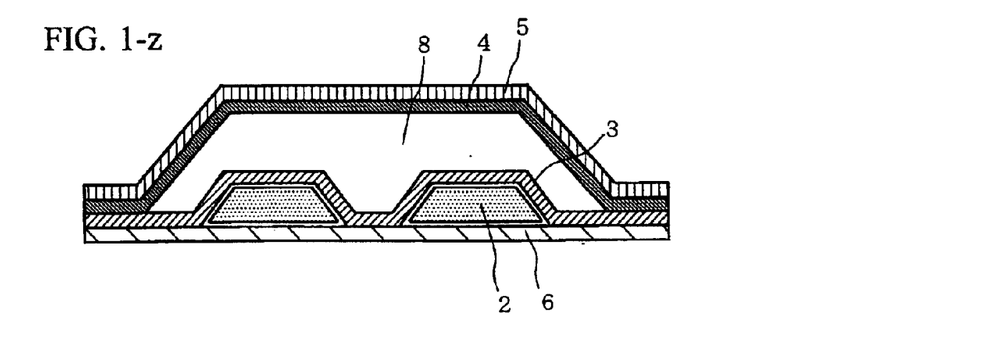

FIG. 1-$x$ is a plan view of the eye-use steam-generating heating sheet 1A in an example of the present invention when sealed, FIG. 1-$y$ is a cross section thereof when sealed, and FIG. 1-$z$ is a cross section thereof when the steam is released after the eye-use steam-generating heating sheet 1A is removed from its airtight container.

This eye-use steam-generating heating sheet 1A comprises a steam-generating composition 2 that fills a space formed between a backing sheet 6 and a first moisture-permeable sheet 3, and the first moisture-permeable sheet 3 is covered first with a second moisture-permeable sheet 4 and then with a top sheet 5. This sheet 1A is applied over the eyes and the area surrounding the eyes. The first moisture-permeable sheet 3 and the second moisture-permeable sheet 4 here are joined at their peripheral edges 3a and 4a, such that the inside of the joining portion can be separated from each other, whereby a steam accumulation space 8 can be formed between these sheets in the state where the eye-use steam-generating heating sheet 1A is emitting water vapor. The joining portion between the first moisture-permeable sheet 3 and the second moisture-permeable sheet 4 is preferably not provided over the portion filled with the steam-generating composition 2, but is not limited to just the peripheral edges 3a and 4a.

This eye-use steam-generating heating sheet 1A is sealed in an airtight container 7 for storage.

In the present invention, as will be discussed in detail below, the makeup of the steam-generating composition 2, the structure of the sheet covering the steam-generating composition 2, the moisture permeability of the various sheets, and so forth are adjusted so that when the eye-use steam-generating heating sheet 1A is taken out from the airtight container 7 and applied to eyes on top sheet 5 side, heat is quickly generated by the oxidation reaction of the steam-generating composition 2, but this exothermic reaction stops by itself and the temperature drops after a specific length of time, so the skin is not burned at the application site, the wearer experiences no pain as caused by heat irritation or the like, and plenty of steam is supplied to the application site.

More specifically, the surface temperature of the eye-use steam-generating heating sheet 1A reaches 35 to 65° C. due to the release of steam from this surface within 5 minutes after removing the eye-use steam-generating heating sheet 1A from airtight container. If the surface temperature of the eye-use steam-generating heating sheet 1A exceeds 65° C. within 5 minutes after removing the eye-use steam-generating heating sheet 1A from airtight container, there is a risk of burns.

On the other hand, if the surface temperature of the eye-use steam-generating heating sheet 1A does not reach 35° C. within 5 minutes after removing the eye-use steam-generating heating sheet 1A from airtight container, the the eye-use steam-generating heating sheet 1A is not warm enough to achieve the eye fatigue relief. In order to achieve relief of eyestrain and relaxation efficacy by warming eyes, it must be kept at the appropriate temperature for at least 5 minutes, and preferably about 10 to 15 minutes. If they are warmed for an extended period, there is conversely the risk of injuring the eyes through a low-temperature burn or the like. In view of this, the eye-use steam-generating heating sheet 1A of the present invention is designed so that the surface temperature will be at least 35° C. for 15 minutes after removing the eye-use steam-generating heating sheet 1A from airtight container 7.

Water vapor is a heat transfer medium, and when steam is released from the eye-use steam-generating heating sheet 1A, the application side is warmed by this steam, but when no steam is being released from the eye-use steam-generating heating sheet 1A, the heat from the steam-generating composition 2 is primarily transferred to the application site in direct contact with the sheet, so the application site is not uniformly warmed. Also, the site where the eye-use steam-generating heating sheet 1A is applied will not be warmed uniformly if the amount of steam released from the eye-use steam-generating heating sheet 1A is less than 10 mg within 10 minutes after removing the eye-use steam-generating heating sheet 1A from airtight container, and instead only the portions in contact with the eye-use steam-generating heating sheet 1A will be warmed, which makes the contact areas more prone to injury by heat irritation, and also prevents enough steam from being supplied to the application site. If not enough steam is released and the application site is not warmed uniformly, the wearer will not fully realize the benefits of using the eye-use steam-generating heating sheet 1A upon removing it from the application site. In view of this, with the eye-use steam-generating heating sheet 1A of the present invention, the total amount of steam released within 10 minutes after removing the eye-use steam-generating heating sheet 1A from airtight container is at least 10 mg, and preferably at least 80 mg.

Figure 2:
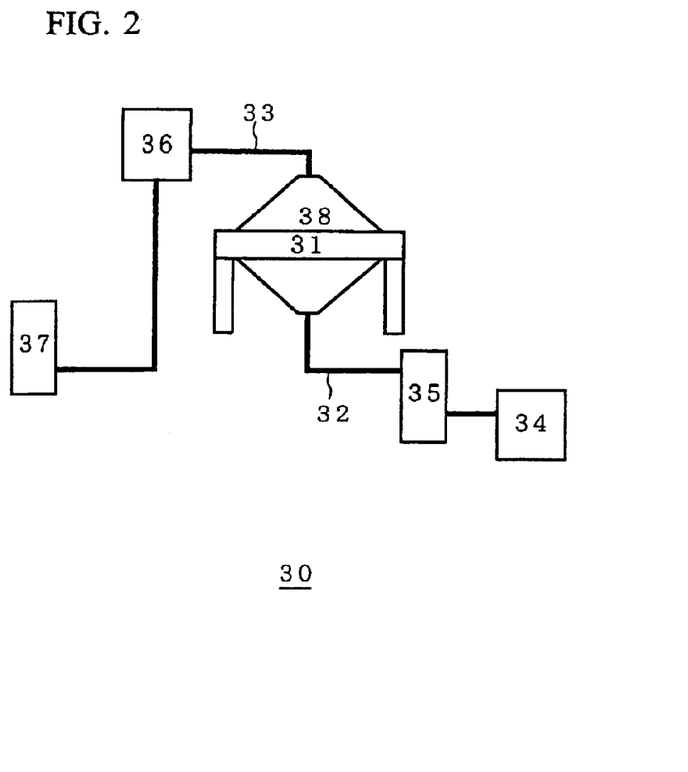
FIG. 2 is a diagram of the apparatus used to measure the surface temperature of the eye-use steam-generating heating sheet and the amount of steam it releases.

The surface temperature and amount of released steam here were measured as follows using the apparatus 30 shown in FIG. 2. The apparatus 30 in FIG. 2 has an aluminum measurement chamber 31 (2.1 L volume), an inflow passage 32 through which dehumidified air (humidity: less than 2%; flow rate: 2.1 L/minute) flows to the lower part of the measurement chamber 31, an outflow passage 33 through which air flows out from the upper part of the measurement chamber 31, an inlet thermometer/hygrometer 34 and an inlet flow meter 35 provided to the inflow passage 32, an outlet thermometer/hygrometer 36 and an outlet flow meter 37 provided to the outflow passage 33, and a thermometer (thermistor) 38 provided inside the measurement chamber 31. The thermometer 38 is one with a temperature resolution of about 0.01° C.

The surface temperature of the eye-use steam-generating heating sheet 1A is measured by taking the eye-use steam-generating heating sheet 1A out of the airtight container 7 at a measurement environment temperature of 30° C. (30±1° C.), placing the sheet 1A in the measurement chamber 31 with its steam release side facing up, placing the thermometer 38 and an attached metal ball (4.5 g) on top of the sheet, and making the measurement. In this state, dehumidified air flows from the bottom, the difference in absolute humidity before and after the air flows into the measurement chamber 31 is found from the temperature and humidity measured with the inlet thermometer/hygrometer 34 and the outlet thermometer/hygrometer 36, and the amount of steam released by the eye-use steam-generating heating sheet 1A is calculated from the flow rate measured with the inlet flow meter 36 and the outlet flow meter 37.

In the present invention, a composition composed of (1) a metal that serves as the main heat generating agent, (2) water that serves as the raw material for generating steam, (3) a water retention agent, (4) a reaction promoter composed of a water-soluble salt, and (5) other reaction promoters is used as the steam-generating composition 2.

Examples of the metal (1) here include iron, aluminum, zinc, and copper.

Examples of the water retention agent (3) include vermiculite, calcium silicate, silica gel, alumina, pulp, and water-absorbent polymers.

Examples of reaction promoters composed of a water-soluble salt (4) include sodium chloride, potassium chloride, and other chlorides of alkali metals; and calcium chloride, magnesium chloride, and other chlorides of alkaline earth metals.

Examples of other reaction promoters (5) include activated carbon, carbon black, and graphite.

These components (1) to (5) can each be used singly or in combinations of two or more types.

In the present invention, it is important for the steam-generating composition 2 to have sufficient capability of generating steam so that the surface temperature and the amount of released steam of the eye-use steam-generating heating sheet 1A after being taken out of the package 7 will be as above. It is preferable here for the steam-generating composition 2 to be prepared as a powder with a high water content, and the compositional range thereof is preferably (1) 20 to 80 wt % metal (such as iron powder), (2) 20 to 60 wt % water, (3) 3 to 25 wt % water retention agent (water-absorbent polymer, vermiculite, etc.), (4) 0.3 to 12 wt % reaction promoter composed of a water-soluble salt, and (5) 3 to 25 wt % other reaction promoters (activated carbon, etc.).

The place to be filled with the steam-generating composition 2 is preferably located so that heating steam can be supplied to both the left and right eyes when the eye-use steam-generating heating sheet 1A is applied to the application site, and the filling amount is preferably 2 to 7 g per site covering one eye. The filling rate of the steam-generating composition is preferable 0.1 to 4.0 g/cm$^2$ from the standpoint of temperature control and achieving a uniform temperature.

When the eye-use steam-generating heating sheet 1A is seen in plan view, the surface area S1 of the portions filled with the steam-generating composition 2 (the portions hatched with lines going down to the left in FIG. 1-$x$) and the surface area S2 of the portion where the steam accumulation space 8 is formed (the portion hatched with lines going down to the right in FIG. 1A) should be such that S2/S1=1.5/1 to 5/1, with a range of 1.5/1 to 4/1 being particularly favorable. If this ratio is too small, the steam accumulation space 8 will not be extensive enough and not enough steam can be accumulated, so the temperature control effect will be diminished. On the other hand, it is also undesirable for this ratio to be too large, because the steam accumulation space 8 will be so thin that the temperature control effect will be diminished.

The backing sheet 6 is provided so that steam from the steam-generating composition 2 will be released only from one side of the eye-use steam-generating heating sheet 1A, which is formed as a thin sheet, and therefore this backing sheet 6 must be moisture-impermeable. In terms of joining to the first moisture-permeable sheet 3 in the course of manufacturing the eye-use steam-generating heating sheet 1A, it is preferable for the backing sheet 6 to be made of a sheet material that can be heat fused. Examples of this backing sheet 6 include (1) a sheet composed of polyethylene, polypropylene, polyester, polystyrene, or the like, (2) a laminated sheet composed of a nonwoven cloth or synthetic paper and a film material such as polyethylene, polypropylene, polyester, or polystyrene.

The first moisture-permeable sheet 3 is highly permeable to moisture, with a moisture permeability of at least 600 g/m$^2$/24 hrs, and preferably at least 1200 g/m$^2$/24 hrs, so that the steam-generating composition 2 will take in oxygen from the outside, an exothermic reaction will occur, and steam will be released into the steam accumulation space 8.

The moisture permeability here is measured as set forth in ASTM E-96-80D (Standard Test Methods for Water Vapor Transmission of Materials), at a measurement environment temperature of 32.2° C. and a measurement environment humidity of 50% RH.

The first moisture-permeable sheet 3 also has a water resistance of at least 400 mm, and preferably at least 500 mm, so as to prevent the leakage of the steam-generating composition 2 or reaction products thereof, such as water-soluble components (salts, iron ions, etc.) and colloidal substances (iron hydroxide, etc.). If the water resistance is less than 400 mm, serious problems such as eye irritation, cornea damage, or blindness could occur if such compounds leaked from the steam-generating composition 2 into the eyes.

Water resistance here is measured as set forth in JIS L-1092 (Water Resistance Test, Hydrostatic Pressure A Method) at a measurement environment temperature of 20±2° C. (standard apparatus speed: 60±3 cm/min).

The material from which the first moisture-permeable sheet 3 is made is preferably hydrophobic so as to prevent the leakage of the steam-generating composition and reaction products thereof.

The first moisture-permeable sheet 3 is preferably one in which the pores distributed throughout the sheet have a diameter of 0.2 μm or less, and the water activity is 0.6 or less. If the pore diameter is kept to 0.2 μm or less, then even if microorganisms such as aerobic bacteria, yeasts, and molds should infiltrate the space bounded by the first moisture-permeable sheet 3 and the backing sheet 6, these can be prevented from leaving this space. Bacteria generally do not proliferate at a water activity of 0.9 or less, yeasts do not proliferate at a water activity of 0.8 or less, and molds do not proliferate at a water activity of 0.7 or less, so the proliferation of molds and other such microbes can be prevented and the application site can be maintained in a healthy state by keeping the water activity of the first moisture-permeable sheet 3 to 0.6 or less. The water activity can be measured with a Rotonics water activity meter (20° C., 40% RH).

It is preferable for the first moisture-permeable sheet 3 to be made of a heat-fusible sheet because this will facilitate joining to the above-mentioned backing sheet 6.

Specific examples of the material that makes up the first moisture-permeable sheet 3 include (1) nonwoven cloth, (2) synthetic paper, (3) a laminated sheet of nonwoven cloth and paper or synthetic paper, (4) a sheet made from chemical fibers and pulp by papermaking process, (5) a porous film, (6) a laminated or embossed sheet of nonwoven cloth and a porous film, (7) a laminated or embossed sheet of synthetic paper and a porous film, and (8) a laminated or embossed sheet of two or more nonwoven cloths or two or more sheets of synthetic paper, all with a moisture permeability of at least 600 g/m$^2$/24 hrs and a water resistance of at least 400 mm. Of these sheets, one whose raw material is polyethylene, polypropylene, polyester, polystyrene, or the like is preferred because of its highly hydrophobic properties.

Meanwhile, the second moisture-permeable sheet 4 is provided so that the steam released from the steam-generating composition 2 will first fill the space between the second moisture-permeable sheet 4 and the first moisture-permeable sheet 3, resulting in more uniform heating of the surface of the second moisture-permeable sheet 4, and so that this steam will then permeate evenly through the entire surface of the second moisture-permeable sheet 4. Accordingly, the second moisture-permeable sheet 4 is provided so that it can be separated from the first moisture-permeable sheet 3, thereby producing the steam accumulation space 8, and the moisture permeability thereof should be 700 to 3000 g/m$^2$/24 hrs, and preferably 1200 to 3000 g/m$^2$/24 hrs. This moisture permeability is measured by the method discussed above. If the moisture permeability is less than 700 g/m$^2$/24 hrs, it will be difficult for the steam-generating composition 2 to take in oxygen from the outside, the exothermic reaction will not proceed very well, steam will be generated only slowly, and the steam will not sufficiently accumulate in the space between the first moisture-permeable sheet 3 and the second moisture-permeable sheet 4. Conversely, if the moisture permeability is over 3000 g/m$^2$/24 hrs, the steam that permeates the first moisture-permeable sheet 3 will immediately permeate the second moisture-permeable sheet 4 as well, not enough steam will accumulate in the space between the first moisture-permeable sheet 3 and the second moisture-permeable sheet 4, and the heating cannot be made uniform.

It is also preferable, in terms of the hygiene of the application site, for the second moisture-permeable sheet 4 to have a water activity of 0.6 or less, and it is preferable for it to be made of a heat-fusible sheet in order to facilitate joining to the first moisture-permeable sheet 3.

Specific examples of the material that makes up the second moisture-permeable sheet 4 include (1) nonwoven cloth, (2) synthetic paper, (3) a laminated sheet of nonwoven cloth and paper or synthetic paper, (4) a sheet made from chemical fibers and pulp by papermaking process, (5) a porous film, (6) a laminated or embossed sheet of nonwoven cloth and a porous film, (7) a laminated or embossed sheet of synthetic paper and a porous film, and (8) a laminated or embossed sheet of two or more nonwoven cloths or two or more sheets of synthetic paper, all with a moisture permeability of 700 to 3000 g/m$^2$/24 hrs. It is preferable for the raw material that makes up the sheet to be polyethylene, polypropylene, polyester, polystyrene, or the like because of the highly hydrophobic properties thereof.

The top sheet 5 is provided in order to form a gap between the second moisture-permeable sheet 4 and the skin of the application site. If the second moisture-permeable sheet 4 comes into direct contact with the skin, and condensation water is present at the interface thereof, not enough oxygen will be supplied for the oxidation reaction of the steam-generating composition 2. The top sheet 5 also serves to enhance the feel of the product, so that the wearer does not experience discomfort due to stickiness and so forth caused by condensation water.

Since the top sheet 5 is the outermost layer of the eye-use steam-generating heating sheet 1A, is preferable has a higher moisture permeability than the second moisture-permeable sheet 4, having a moisture permeability of at least 2500 g/m$^2$/24 hrs, and preferably at least 3000 g/m$^2$/24 hrs, so as not to hinder the passage of steam that has permeated the first moisture-permeable sheet 3 and the second moisture-permeable sheet 4.

It is also preferable for the top sheet 5 to have a water activity of 0.6 or less, as this will improve the hygiene of the eye site, and to be a heat-fusible sheet, as this will facilitate joining to the second moisture-permeable sheet 4.

Specific examples of the material that makes up the top sheet 5 include (1) nonwoven cloth, (2) a perforated film, (3) a laminated sheet of nonwoven cloth and paper or synthetic paper, (4) a laminated or embossed sheet of nonwoven cloth and a perforated film, (5) a laminated or embossed sheet of synthetic paper and a perforated film, and (6) a laminated or embossed sheet of two or more nonwoven cloths or two or more sheets of synthetic paper, preferably all with a moisture permeability of at least 2500 g/m$^2$/24 hrs. It is preferable for the raw material that makes up the sheet to be polyethylene, polypropylene, polyester, polystyrene, or the like because of the highly hydrophobic properties thereof.

The package 7 is used so that even if the steam-generating composition 2 is shut off from the oxygen and moisture on the outside and the product then stored for an extended period, the makeup of the steam-generating composition 2 will not change, and the ability to generate steam will remain stable. Accordingly, the package 7 is made from a material having a lower oxygen permeability and moisture permeability than those of packages that seal in what are commonly known as chemical pocket warmers, and preferably the oxygen permeability of the package 7 will be 0.1 cc/m$^2$/24 hrs or less, and its moisture permeability will be 0.1 g/m$^2$/24 hrs or less.

The oxygen permeability here is measured by the method for testing the gas permeability of plastic films and sheets set forth in JIS K 7126-A, at a measurement environment temperature of 23±2° C.

The moisture permeability is measured by the method for testing the moisture permeability of moisture-proof packaging materials set forth in JIS Z 0208, at a measurement environment temperature of 40±0.5° C. and a measurement environment humidity (relative humidity) of 90±2%.

In particular, if a resin film or the like laminated with aluminum foil, an aluminum alloy foil, or the like is used as the package 7, the oxygen permeability will be sufficiently low and the permeation of oxygen from the outside can be substantially blocked, so when the eye-use steam-generating heating sheet 1A is sealed in the package 7, even if aerobic bacteria, yeast, mold, or the like should get in, the steam-generating composition 2 will consume the oxygen inside the package 7, making it impossible for the aerobic bacteria, yeast, mold, or the like to survive, which is preferable in terms of maintaining hygiene at the application site.

The sheet materials that make up the eye-use steam-generating heating sheet 1A consist of the above-mentioned backing sheet 6, first moisture-permeable sheet 3, second moisture-permeable sheet 4, and top sheet 5, and no other paper, nonwoven cloth, or the like is necessary as a temperature buffer. Therefore, in a state in which the steam accumulation space 8 has not been formed between the first moisture-permeable sheet 3 and the second moisture-permeable sheet 4, the eye-use steam-generating heating sheet 1A can be in the form of a thin sheet with a maximum thickness of 2.5 to 5 mm and a thickness of 0.5 to 1.2 mm at the portion not filled with the steam-generating composition.

Figure 3:
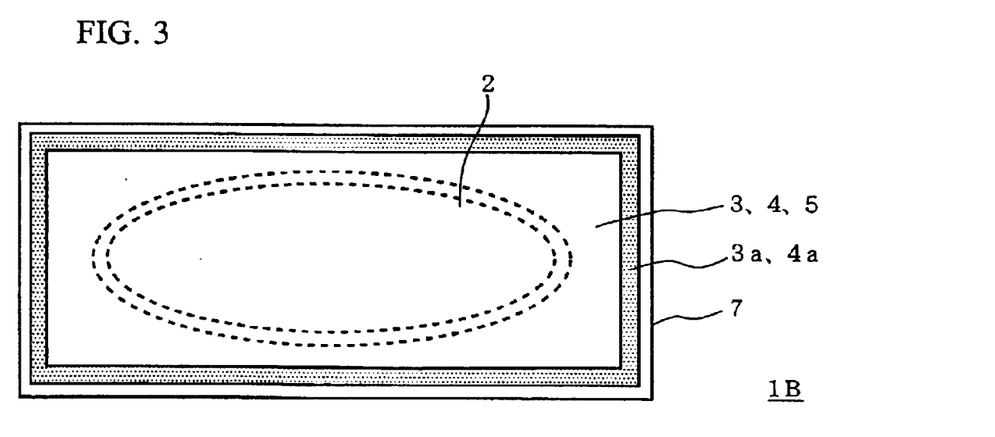
FIG. 3 is a plan view of the eye-use steam-generating heating sheet of the present invention.

The eye-use steam-generating heating sheet of the present invention can assume various other aspects besides that shown in the drawings. There are no particular restrictions on the shape and size of the space filled with the steam-generating composition 2. Further, the number of spaces filled with the steam-generating composition 2 is not limited to two as shown sheet 1A as long as the required temperature setting range and steam quantity can be achieved, and there may instead be only one such space as in the eye-use steam-generating heating sheet 1B in FIG. 3, or there may be three or more spaces as in the eye-use steam-generating heating sheet 1C in FIG. 4 and the eye-use steam-generating heating sheet 1D in FIG. 5.

Also, the water resistance of the first moisture-permeable sheet 3 was set to be at least 400 mm with the eye-use steam-generating heating sheet 1A, but the water resistance of the second moisture-permeable sheet 4 may be set to be at least 400 mm instead of that of the first moisture-permeable sheet 3, or along with that of the first moisture-permeable sheet 3.

EXAMPLES

Example 1

The eye-use steam-generating heating sheet 1A was produced as follows.

A hydrous water retention agent was prepared by adding 46.5 weight parts 3% salt water to 7 weight parts water-absorbent polymer (Aquapearl A3, made by Diapolyacrylate), 10 weight parts activated carbon (Carboraffin, made by Takeda Pharmaceutical), and 7 weight parts vermiculite (Hiruishi CW-1, made by Kakiuchi Material). 70.5 weight parts of this hydrous water retention agent was mixed with 29.5 weight parts reduced iron powder (RKH, made by Dowa Iron Powder) to obtain a steam-generating composition A.

Meanwhile, a substantially rectangular, moisture-impermeable polyethylene sheet (basis weight 33 g/m$^2$) formed with a depression to fit the nose and measuring 20 cm wide and 10 cm high (used as a backing sheet) was put together with a sheet of moisture-permeable synthetic paper (moisture permeability 2000 g/m$^2$/24 hrs, water resistance 700 mm, basis weight 40 g/m$^2$) (used as the first moisture-permeable sheet), these were heat-fused so as to form two portions (for the two eyes) 5 cm in diameter and to be filled with a steam-generating composition, and each portion was filled with 3.0 g of the above-mentioned steam-generating composition A and sealed.

The same moisture-permeable synthetic paper as used for the first moisture-permeable sheet was laminated as a second moisture-permeable sheet over the first moisture-permeable sheet, then a polyethylene nonwoven cloth (moisture permeability 2800 g/m$^2$/24 hrs, basis weight 30 g/m$^2$) was laminated as a top sheet, and the outer periphery of these components was heat-fused to form a steam accumulation space between the first moisture-permeable sheet and second moisture-permeable sheet, resulting in a steam-generating heating sheet for the eyes. The thickness of the portions of this eye-use steam-generating heating sheet that were filled with the steam-generating composition was 4 mm, and the thickness of the unfilled portion was 1 mm.

The eye-use steam-generating heating sheet obtained in this manner was put into an aluminum laminate pouch (oxygen permeability 0.1 cc/m$^2$/24 hrs or less, moisture permeability 0.1 g/m$^2$/24 hrs or less), and this pouch was sealed and stored.

Example 2

Figure 4:
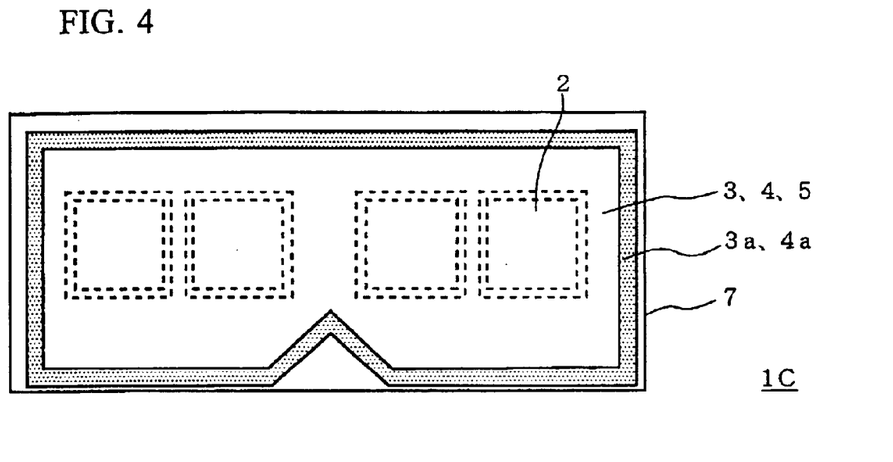
FIG. 4 is a plan view of the eye-use steam-generating heating sheet of the present invention.
Figure 5:
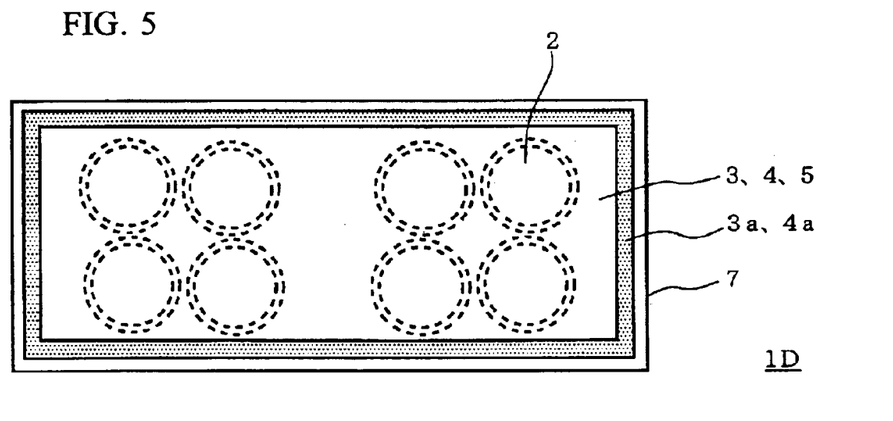
FIG. 5 is a plan view of the eye-use steam-generating heating sheet of the present invention.

The eye-use steam-generating heating sheet 1C shown in FIG. 4 was produced as follows.

A hydrous water retention agent was prepared by adding 23 weight parts 4.3% salt water to 7 weight parts water-absorbent polymer, 10 weight parts activated carbon, and 7 weight parts vermiculite. 47 weight parts of this hydrous water retention agent was mixed with 53 weight parts reduced iron powder to obtain a steam-generating composition B. The constituent components of this steam-generating composition B were the same as those used for the above-mentioned steam-generating composition A.

Meanwhile, a substantially rectangular, moisture-impermeable polyethylene sheet (basis weight 33 g/m$^2$) formed with a depression to fit the nose and measuring 20 cm wide and 10 cm high (used as a backing sheet) was put together with a moisture-permeable nonwoven cloth (moisture permeability of 2600 g/m$^2$/24 hrs and a water resistance of 500 mm; an embossed sheet produced by laminating a moisture-permeable nonwoven cloth with a basis weight of 20 g/m$^2$ (Syntex SB made by Mitsui Chemical), a moisture-permeable nonwoven cloth with a basis weight of 30 g/m$^2$ (Syntex MB made by Mitsui Chemical), and another moisture-permeable nonwoven cloth with a basis weight of 20 g/m$^2$ (Syntex SB made by Mitsui Chemical) for use as the first moisture-permeable sheet. These were heat-fused so as to form four square portions (two for each eye) measuring 3 cm per side and to be filled with a steam-generating composition, and each portion was filled with 2.0 g of the above-mentioned steam-generating composition B and sealed.

The same moisture-permeable nonwoven cloth as used for the first moisture-permeable sheet was laminated as a second moisture-permeable sheet over the first moisture-permeable sheet, then a polyethylene nonwoven cloth (moisture permeability 2900 g/m$^2$/24 hrs, basis weight 25 g/m$^2$) was laminated as a top sheet, and the outer periphery of these components was heat-fused to form a steam accumulation space between the first moisture-permeable sheet and second moisture-permeable sheet, resulting in a steam-generating heating sheet for the eyes. The thickness of the portions of this eye-use steam-generating heating sheet that were filled with the steam-generating composition was 4 mm, and the thickness of the unfilled portion was 1 mm.

The eye-use steam-generating heating sheet obtained in this manner was put into an aluminum laminate pouch (oxygen permeability 0.1 cc/m$^2$/24 hrs or less, moisture permeability 0.1 g/m$^2$/24 hrs or less), and this pouch was sealed and stored.

Example 3

An eye-use steam-generating heating sheet was produced in the same manner as in Example 1, except that a sheet with a moisture permeability of 1400 g/m$^2$/24 hrs (porous polyethylene film, basis weight 20 g/m$^2$) was used as the second moisture-permeable sheet.

Example 4

An eye-use steam-generating heating sheet was produced in the same manner as in Example 1, except that the filled portions were each filled with 2.0 g of the steam-generating composition 2.

Comparative Example 1

An eye-use steam-generating heating sheet was produced in the same manner as in Example 1, except that 8 sheets of paper (basis weight 32 g/m$^2$; J K Wiper, made by Crecia) were further inserted between the first moisture-permeable sheet and the second moisture-permeable sheet for the purpose of temperature control.

Comparative Example 2

An eye-use steam-generating heating sheet was produced in the same manner as in Example 1, except that no second moisture-permeable sheet was used, the top sheet was heat-fused over the entire surface of the first moisture-permeable sheet, so that no steam accumulation space was formed between the first moisture-permeable sheet and the top sheet.

Comparative Example 3

An eye-use steam-generating heating sheet was produced in the same manner as in Example 1, except that a moisture-permeable sheet with a moisture permeability of 140 g/m$^2$/24 hrs (the moisture-permeable sheet used in the Hot & Slim disposable pocket warmer made by Japan Pionics) was used as the second moisture-permeable sheet.

Comparative Example 4

An eye-use steam-generating heating sheet was produced in the same manner as in Example 1, except that a polyethylene nonwoven cloth (basis weight 30 g/m$^2$) with a moisture permeability of 2600 g/m$^2$/24 hrs and a water resistance of 50 mm was used as the first moisture-permeable sheet.

Evaluation

The eye-use steam-generating heating sheets from the various examples and comparative examples were each stored for 3 days in a storage pouch, then taken out to see how long it took the surface temperature of the eye-use steam-generating heating sheet to reach 35° C. after removing the eye-use steam-generating heating sheet 1A from airtight container. The surface temperature 15 minutes and the highest temperature reached within 10 minute after removing the eye-use steam-generating heating sheet 1A from airtight container were measured, and at the same time, the total amount of steam released within 10 minutes was measured. The temperature here was measured using the apparatus in FIG. 2.

The maximum sheet thickness 10 minutes after removing the eye-use steam-generating heating sheet 1A from airtight container was measured in the center of a filled portion. The thickness difference between the steam accumulation space 10 minutes after removing the eye-use-steam-generating heating sheet 1A from airtight container and just after removing the steam-generating heating sheet from airtight container was calculated. Since the formation of the steam accumulation space is easily affected by its external environment, the eye-use steam-generating heating sheet was placed on a heat-insulating material, with the steam release side facing up, and the thickness of the sheet was measured at an environment temperature of about 28° C. in the absence of any air movement.

Meanwhile, each of the eye-use steam-generating heating sheets of the various examples and comparative examples was stored in a storage pouch for 3 days, then taken out of the pouch, immediately after which the eye-use steam-generating heating sheet was placed over the eyes and the surrounding area thereof, the sheet was held in place with an eye mask made from nonwoven cloth and placed over the sheet, and a visual check was made to see if any of the contents had leaked or if there was any powder leakage after the eye-use steam-generating heating sheet had been applied to the application site for 10 minutes after removing the eye-use steam-generating heating sheet 1A from airtight container.

Ten women who suffered from daily eyestrain were selected as panelists, and they used the eye-use steam-generating heating sheets after doing four hours of office work, and evaluated how well the sheets worked.

The results are given in Table 1.

Evaluations were similarly conducted for when the eye-use steam-generating heating sheet in Example 1 was sealed and stored in a package for 30 days in a 50° C. environment, and for when a belt was attached to the ends of the eye-use steam-generating heating sheet and wrapped around the head to hold the sheet in place, instead of using an eye mask made of nonwoven cloth.

TABLE 1

| | Temperature characteristics | | Steam charact. | Condition of eye-use steam-generating heating sheet | | | | |
|---|---|---|---|---|---|---|---|---|
| | Time to reach 35° C. (min.) | Surface temp. 15 min. after open airtight seal (° C.) | Highest temp. reached 10 min. after open airtight seal (° C.) | Total amount of steam released within 10 min. after open airtight seal (mg) | Max. sheet thickness during steam release (mm) | Thickness of steam accumulation space (mm) | Oozing of contents | Powder leakage | Effect |
| Example 1 | 1.5 | 41 | 56 | 300 | 7 | 3 | no | no | good, pleasant feel, relieved strain |
| Example 1 (after storage at 50° C. for 30 days) | 1.5 | 41 | 55 | 290 | 7 | 3 | no | no | same as above |
| Example 1 (belt attached) | 1.5 | 40 | 53 | 280 | 7 | 3 | no | no | same as above |
| Example 2 | 2.5 | 40 | 54 | 290 | 6 | 2 | no | no | same as above |
| Example 3 | 2.5 | 38 | 48 | 180 | 17 | 13 | no | no | same as above |
| Example 4 | 3 | 37 | 45 | 150 | 7 | 3 | no | no | same as above |
| Comparative Example 1 | 6 | 40 | 45 | 150 | 15 | 0 | no | no | warming was irritatingly slow, too thick to fit well over the eyes |
| Comparative Example 2 | 2 | 40 | 50 | 250 | 4 | 0 | no | no | too hot in some places |
| Comparative Example 3 | 6 | 46 | 46 | 10 | 4 | 0 | no | no | too hot in some places |
| Comparative Example 4 | 1.5 | 41 | 56 | 320 | 7 | 3 | yes | yes | impossible to use |

It can be seen from the results in Table 1 that when paper was inserted as a temperature buffer between the first moisture-permeable sheet and the second moisture-permeable sheet (Comparative Example 1), the eye-use steam-generating heating sheet was so thick that it could not be easily applied to the eyes, resulting in an uncomfortable fit, and the warmth is not transfer well. When no steam accumulation space was formed between the first moisture-permeable sheet and the second moisture-permeable sheet (Comparative Example 2), the product felt uncomfortably hot in places, and when the moisture permeability of the second moisture-permeable sheet was too low (Comparative Example 3), the oxygen required for the oxidation reaction of the steam-generating composition was not supplied from the outside and steam was not released. When the water resistance of the first moisture-permeable sheet was too low (Comparative Example 4), the contents oozed out and there was powder leakage. In contrast, in Examples 1 to 4 of the present invention, it can be seen that the amount of steam generation and the temperature elevation rate were both good, the maximum thickness of the eye-use steam-generating heating sheet was low, there was no oozing of the contents or powder leakage, and the product felt good to use.

With the steam-generating heating sheet for the eyes pertaining to the present invention, when steam is released from the sheet is removed from its package, a steam accumulation space is formed between a first moisture-permeable sheet and a second moisture-permeable sheet, so the temperature of the steam supplied to the eyes and their surrounding areas is adjusted to a temperature that is safe and effective at relieving eyestrain and so forth, and since the heating steam is supplied uniformly to the entire application site, there is no need for several layers of temperature buffer. Therefore, the eye-use steam-generating heating sheet can be formed thinner, making it more comfortable, easy to carry around, and more efficient to distribute for sale, and also lowering the manufacturing cost.

Also, with the eye-use steam-generating heating sheet of the present invention, steam is released from the surface of the sheet and the temperature of said surface reaches 35 to 65° C. within 5 minutes after removing the eye-use steam-generating heating sheet 1A from airtight container, the surface temperature 15 minutes after removing the steam-generating sheet from the container is at least 35° C., and the total amount of steam released within 10 minutes after the steam-generating sheet from the container is at least 10 mg, so the eyes and their surrounding areas can be safely and adequately warmed by the heating steam. Therefore, symptoms of eyestrain and dry eyes, such as eye pain, eye fatigue, dryness of the eyes, and itching of the eyes, can be relieved.

The entire disclosure of the specification, claims, summary and drawings of Japanese Patent Application No. 2002-241135 filed on Aug. 21, 2002 is hereby incorporated by reference.

What is claimed is:

1. A steam-generating heating sheet for the eyes comprising:
   i) a steam-generating composition;
   ii) at least a first moisture-permeable sheet and a second moisture-permeable sheet in that order covering said steam-generating composition,
   wherein said first moisture-permeable sheet has a moisture permeability (ASTM E-96-80D method) of at least 600 $g/m^2/24$ hs;
   said second moisture-permeable sheet has a moisture permeability (ASTM E-96-80D method) of 700 to 3000 $g/m^2/24$ hs;
   said first moisture-permeable sheet and said second moisture-permeable sheet are joined at peripheral edges and provided that a steam accumulation space is formed therebetween; and
   at least one of said first or second moisture-permeable sheets covering the steam-generating composition has a water resistance of at least 400 mm.

2. The steam-generating heating sheet for the eyes according to claim 1, wherein a surface temperature of said steam-generating sheet for the eyes reaches 35 to 60° C. within 5 minutes of being opened from a sealed storage state, said surface temperature is at least 35° C. 15 minutes after removing the eye-use steam-generating heating sheet from an airtight container, and the total amount of steam released within 10 minutes after removing the eye-use steam-generating sheet from an airtight container is at least 10 mg.

3. The steam-generating heating sheet for the eyes according to claim 1 or 2, further comprising an airtight container having an oxygen permeability (JIS K 7126-A method) of no more than 0.1 $cc/m^2/24$ hrs, and a moisture permeability (JIS Z 0208 method) is no more than 0.1 $g/m^2/24$ hrs.

4. The steam-generating heating sheet for the eyes according to any of claim 1 or 2, wherein a pore diameter of said first moisture-permeable sheet is no more than 0.2 $\mu m$, and a water activity of said first moisture-permeable sheet and said second moisture permeable sheet is each no more than 0.6.

5. The steam-generating heating sheet for the eyes according to claim 1, wherein a ratio of a surface area of portions filed with said steam-generating composition to a surface area of a portion where said steam accumulation space is formed is from 1.5/1 to 5/1.

6. The steam-generating heating sheet for the eyes according to claim 1, wherein said first moisture-permeable sheet has a moisture permeability of at least 1,200 $g/m^2/24$ hrs.

7. The steam-generating heating sheet for the eyes according to claim 1, wherein said first moisture-permeable sheet has a water resistance of at least 500 mm.

8. The steam-generating heating sheet for the eyes according to claim 1, wherein said second moisture-permeable sheet has a moisture permeability of 1,200 to 3000 $g/m^2/24$ hs.

9. The steam-generating heating sheet for the eyes according to claim 1, further comprising an outermost layer having a higher moisture permeability than that of said second moisture-permeable sheet.

* * * * *